(12) United States Patent
Kreuzer et al.

(10) Patent No.: US 11,544,764 B2
(45) Date of Patent: Jan. 3, 2023

(54) METHOD OF GENERATING USER FEEDBACK INFORMATION TO ENHANCE PRODUCT USE RESULTS

(71) Applicant: The Procter & Gamble Company, Cincinnati, OH (US)

(72) Inventors: Melissa Ann Kreuzer, Loveland, OH (US); Faiz Feisal Sherman, Mason, OH (US); Justin Gregory Parker, Montgomery, OH (US); Jonathan Michael Martin, Covington, KY (US); Jonathan Livingston Joyce, Crestview Hills, KY (US); Paris Nicolle Jackson, Forest Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/897,793

(22) Filed: Jun. 10, 2020

(65) Prior Publication Data
US 2020/0387942 A1 Dec. 10, 2020

Related U.S. Application Data

(60) Provisional application No. 62/859,427, filed on Jun. 10, 2019.

(51) Int. Cl.
*G06Q 30/00* (2012.01)
*G06Q 30/06* (2012.01)
(Continued)

(52) U.S. Cl.
CPC ......... *G06Q 30/0631* (2013.01); *G01D 21/02* (2013.01); *G06N 20/00* (2019.01);
(Continued)

(58) Field of Classification Search
CPC .......... G06Q 30/0631; G06Q 30/0271; G06Q 30/0201; G06Q 30/0255; G06Q 30/0282;
(Continued)

(56) References Cited

U.S. PATENT DOCUMENTS 5,858,333 A    1/1999  Winston et al.
8,071,076 B2   12/2011 Nathoo
(Continued)

FOREIGN PATENT DOCUMENTS

JP    2009539719 A    11/2009
JP    2010172256 A     8/2010
(Continued)

OTHER PUBLICATIONS

US 9,682,022 B2, 06/2017, Solan (withdrawn)
(Continued)

*Primary Examiner* — Sun M Li
(74) *Attorney, Agent, or Firm* — Alexandra S. Anoff

(57) ABSTRACT

A skin care computing device that includes a user interface, a camera, a speaker, a communication interface, and a personal care assistant application. The personal care assistant application can identify personal care products being used by a user and product use event data describing the use of a personal care product by the user, such as the date and time of the use, the duration and frequency of the use, and the manner in which the personal care product is being used. Then the personal care assistant application generates user feedback information for the personal care product based on the product use event data, previous instances of product use event data, and/or user profile data for the user.

13 Claims, 7 Drawing Sheets

(51) Int. Cl.

| | |
|---|---|
| *G06Q 30/02* | (2012.01) |
| *G16H 20/70* | (2018.01) |
| *G06N 20/00* | (2019.01) |
| *G01D 21/02* | (2006.01) |
| *G10L 25/51* | (2013.01) |
| *H04L 67/306* | (2022.01) |

(52) U.S. Cl.
CPC ..... *G06Q 30/0201* (2013.01); *G06Q 30/0255* (2013.01); *G06Q 30/0271* (2013.01); *G06Q 30/0282* (2013.01); *G10L 25/51* (2013.01); *G16H 20/70* (2018.01); *H04L 67/306* (2013.01)

(58) Field of Classification Search
CPC ........ G16H 20/70; G06N 20/00; G01D 21/02; G10L 25/51; H04L 67/306; A45D 44/005
USPC ...................................................... 705/26.7
See application file for complete search history.

(56) References Cited

U.S. PATENT DOCUMENTS

| | | | |
|---|---|---|---|
| 8,728,446 | B2 | 5/2014 | Hurwitz |
| 9,304,736 | B1 | 4/2016 | Whiteley |
| 9,492,379 | B2 | 11/2016 | Park et al. |
| 9,656,102 | B2 | 5/2017 | Vaccaro et al. |
| 9,750,669 | B2 | 9/2017 | Solan |
| 10,092,779 | B2 | 10/2018 | Fontana et al. |
| 10,095,688 | B1 | 10/2018 | Schilling et al. |
| 10,517,836 | B2 | 12/2019 | Darcy |
| 10,526,570 | B2 | 1/2020 | Dreher |
| 2002/0187108 | A1 | 12/2002 | Rajaiah et al. |
| 2011/0027328 | A1 | 2/2011 | Baig et al. |
| 2012/0053108 | A1 | 3/2012 | Glenn, Jr. |
| 2013/0101652 | A1 | 4/2013 | Boyd et al. |
| 2013/0172226 | A1 | 7/2013 | Dreher |
| 2015/0072915 | A1 | 3/2015 | Dreher |
| 2016/0101026 | A1 | 4/2016 | Pratt et al. |
| 2017/0024589 | A1 | 1/2017 | Schumacher |
| 2017/0238692 | A1 | 8/2017 | Sarubbo |
| 2017/0270593 | A1* | 9/2017 | Sherman ............ G06Q 30/0251 |
| 2017/0340267 | A1* | 11/2017 | Shen .................... G06V 10/751 |
| 2018/0014777 | A1* | 1/2018 | Amir .................... A61B 5/4839 |
| 2018/0223225 | A1 | 8/2018 | Tan et al. |
| 2018/0258555 | A1 | 9/2018 | Glenn, Jr. et al. |
| 2018/0333339 | A1 | 11/2018 | Hamersky |
| 2019/0043064 | A1 | 2/2019 | Chin et al. |
| 2019/0080385 | A1* | 3/2019 | Horton ............... G06Q 30/0203 |
| 2019/0233970 | A1 | 8/2019 | Reed |
| 2019/0233974 | A1 | 8/2019 | Reed |
| 2019/0237194 | A1* | 8/2019 | Salvi ...................... G16H 10/60 |
| 2019/0343732 | A1 | 11/2019 | Mao |
| 2019/0343733 | A1 | 11/2019 | Payne |
| 2019/0343735 | A1 | 11/2019 | Swartz |
| 2019/0343737 | A1 | 11/2019 | Baig |
| 2019/0344953 | A1 | 11/2019 | Trokhan |
| 2020/0143655 | A1 | 5/2020 | Gray et al. |
| 2020/0388374 | A1 | 12/2020 | Kreuzer et al. |
| 2020/0390662 | A1 | 12/2020 | Sagel |
| 2020/0390668 | A1 | 12/2020 | Hartsig et al. |
| 2020/0390680 | A1 | 12/2020 | Sagel et al. |

FOREIGN PATENT DOCUMENTS

| | | | |
|---|---|---|---|
| JP | 2016539873 | A | 12/2016 |
| JP | 2016540701 | A | 12/2016 |
| WO | 2005004824 | A1 | 1/2005 |
| WO | 2007124521 | A1 | 11/2007 |
| WO | 2008080146 | A1 | 7/2008 |
| WO | 2012003349 | A2 | 1/2012 |
| WO | 2015034975 | A1 | 3/2015 |
| WO | 2016001248 | A1 | 1/2016 |

OTHER PUBLICATIONS

R. Iwabuchi et al., "Proposal of recommender system based on userevaluation and cosmetic ingredients," 2017 International Conference on Advanced Informatics, Concepts, Theory, and Applications (ICAICTA), 2017, pp. 1-6, doi: 10.1109/ICAICTA.2017. 8090967. (Year: 2017).*

E. Freudenthal et al., "Suitability of NFC for Medical Device Communication and Power Delivery," 2007 IEEE Dallas Engineering in Medicine and Biology Workshop, 2007, pp. 51-54, doi: 10.1109/EMBSW.2007.4454171. (Year: 2007).*

S. Tangsripairoj, K. Khongson, P. Puangnak and Y. Boonserm, "SkinProf: An Android Application for Smart Cosmetic and Skincare Users," 2018 15th International Joint Conference on Computer Science and Software Engineering (JCSSE), 2018, pp. 1-6, doi: 10.1109/JCSSE.2018.8457178. (Year: 2018).*

PCT Search Report and Written Opinion for PCT/US2020/070131 dated Sep. 9, 2020, 13 pages.

All Office Actions, U.S. Appl. No. 16/898,466.

All Office Actions, U.S. Appl. No. 16/898,468.

All Office Actions. U.S. Appl. No. 17/037,789.

All Office Actions, U.S. Appl. No. 16/897,316.

Darum sollten Sie niemals ihre Zahnburste vorm Putzen nass machen Gesundheit—Anonymous retrieved from the Internat at https://www.tz/de/leben/gesundheit/darum-duerfen-niemals-ihre-zahnbuerste-vorm-putzen-nass-machen-zr-9398685.html on Nov. 27, 2017.

Dental Finger Tooth Cleaner anonymous—retrieved from www.gnpd.com on Dec. 5. 2020.

Oral Care Kit retrieved from www.gnpd.com on Apr. 18, 2019.

Oral Hygiene Kit retrieved from www.gnpd.com—abstract Jun. 17, 2015.

Travel Kit—anonymous—retrieved from www.gnpd.com dated Feb. 12, 2019.

All Office Actions; U.S. Appl. No. 17/529,319, dated Nov. 18, 2021.

U.S. Appl. No. 17/529,319, filed Nov. 18, 2021, to first inventor et al.

All Office Actions; U.S. Appl. No. 17/717,391, dated Apr. 11, 2022.

U.S. Appl. No. 17/717,391, filed Apr. 11, 2022, to Dana Elizabeth Hartsig et al.

All Office Actions; U.S. Appl. No. 17/745,923, filed May 17, 2022.

U.S. Appl. No. 17/745,923, filed May 17, 2022, to Paul Albert Sagel.

* cited by examiner

| User ID 302 | Name 304 | Address 306 | DOB 308 | Personal Care Goals 310 | Reported Issues 312 | Rewards Points 314 |
|---|---|---|---|---|---|---|
| 1 | John Doe | 123 Main Street, Cincinnati, OH | 09/09/99 | Reduce Hair Loss | Hair Loss | 542 |
| 2 | Jane Smith | 456 State Street, Boston, MA | 03/07/72 | Improve Skin Texture | Dry Skin | 8,764 |
| | | | | | | |

| User ID 402 | Product 404 | Date/Time 406 | Duration 408 | Manner of Use 410 |
|---|---|---|---|---|
| 2 | Olay Total Effects Whip Face Moisturizer | 07/26/2019 at 9:14 a.m. | 1 minute | Rubbed unevenly on parts of face |
| 2 | SK-II Facial Treatment Mask | 07/22/2019 at 9:37 a.m. | 7 minutes | Placed mask on face and rinsed off |
| 2 | Olay Total Effects Whip Face Moisturizer | 07/14/2019 at 7:15 p.m. | 30 seconds | Rubbed evenly all over face |

| Recommendation |
|---|
| "Use a skin care product with sunscreen to protect against harmful UV rays" |
| "In the past month you have been moisturizing about twice a week. Make sure you moisturize every day" |
| "Don't forget to replace your skin care product after 5 uses" |
| "Buy OLAY Wrinkle Repair Serum to use along with your moisturizer" |
| "You have earned 200 rewards points for maintaining proper skin care habits" |

FIG. 5

METHOD OF GENERATING USER FEEDBACK INFORMATION TO ENHANCE PRODUCT USE RESULTS

TECHNICAL FIELD

The present disclosure generally relates to skin care systems, and, more particularly, to a skin care assistant for identifying instances of use of skin care products and providing feedback to a user to enhance the user's experience with the skin care products.

BACKGROUND

Typically, home assistant devices or other computing devices collect data from network-enabled devices to enhance the users' experiences with the network-enabled devices. For example, a home assistant device may learn a user's habits based on the user's interactions with other network-enabled devices, such as smart lights, a smart TV, a smart heating and air conditioning system, etc. The home assistant device may then automatically control the network-enabled devices according to the learned habits. In another example, a smart TV may provide indications of the user's watching habits to a remote server that provides recommendations on similar TV shows and movies to those the user is currently watching.

However, such devices do not have similar ways of learning habits based on user interactions with devices which are not network-enabled, such as skin care products. While users interact with skin care products, such as makeup, shampoo, conditioner, moisturizer, hand cream, face cream, toothbrushes, mouthwash, facial cleansers, etc., on a daily basis, computing devices do not collect usage data based on users' interactions with these products to enhance the user experience. Accordingly, users do not know if they are using the products correctly and at the appropriate rate or for the appropriate amount of time.

SUMMARY

The present disclosure is directed to a computing device for providing feedback to a user regarding skin care products. The device comprises a user interface; a communication interface; one or more processors; and a non-transitory computer-readable memory coupled to each of the processors, the user interface, and the communication interface. The non-transitory computer-readable memory comprises instructions that, when executed by the one or more processors, cause the computing device to obtain an indication of product usage of a skin care product by a user; identify the skin care product based on the obtained indication of product usage of the skin care product; obtain product use event data associated with the user for the skin care product, wherein the product use event data is related to product usage of the skin care product over time; obtain user profile data of the user; generate user feedback information to assist the user with the product usage of the skin care product or related skin care products based on the product use event data for the skin care product and the user profile data for the user; and provide the user feedback information via the user interface or the communication interface to a mobile device of the user.

BRIEF DESCRIPTION OF THE DRAWINGS

FIG. 3 illustrates an example data table including user profile data.

FIG. 4 illustrates another example data table including product use event data.

FIG. 5 illustrates an example of providing feedback to the user.

DETAILED DESCRIPTION

Figure 1:
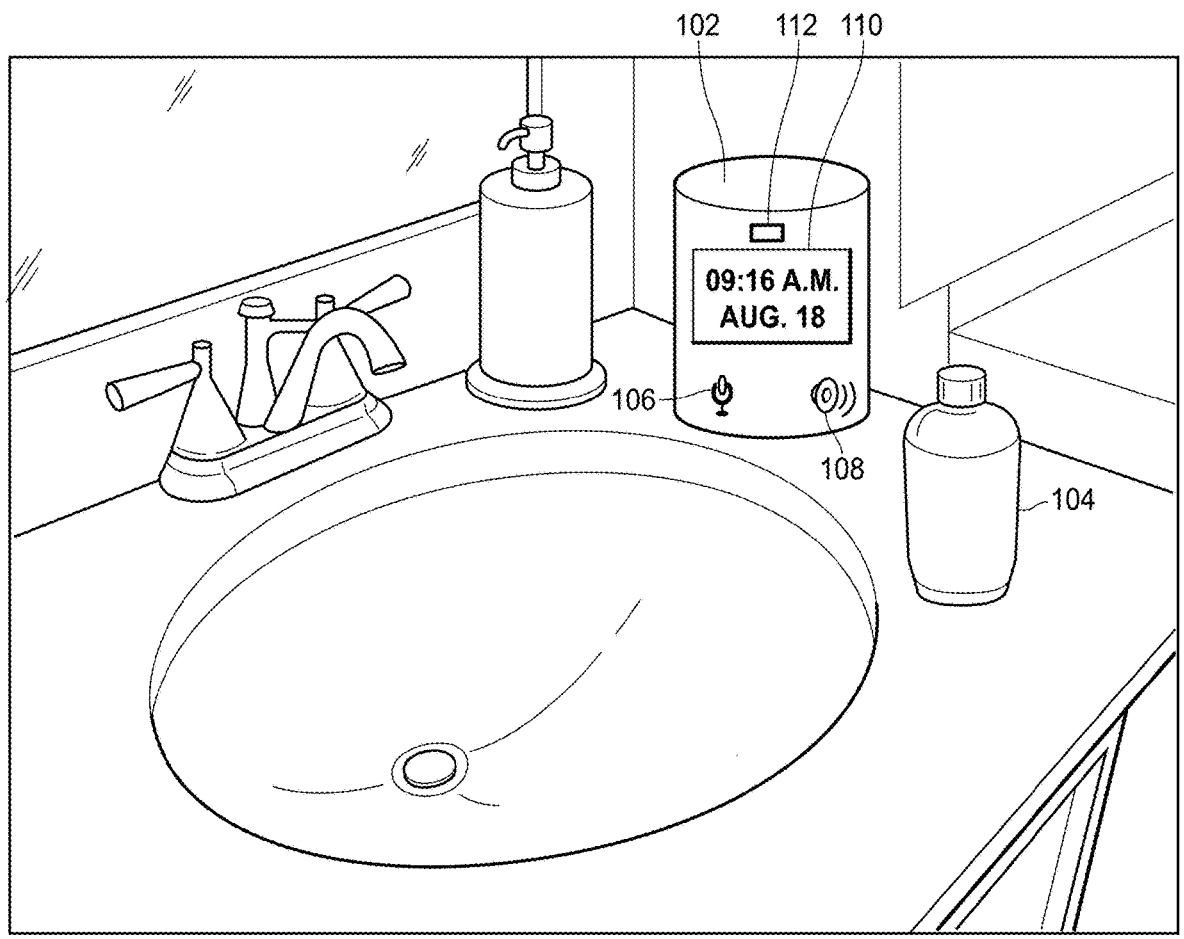
FIG. 1 illustrates an example of the present system.

Reference within the specification to "embodiment(s)" or the like means that a particular material, feature, process, process step, structure and/or characteristic described in connection with the embodiment is included in at least one embodiment, optionally a number of embodiments, but it does not mean that all embodiments incorporate the material, feature, process, process step, structure, and/or characteristic described. Furthermore, materials, features, processes, process steps, structures and/or characteristics may be combined in any suitable manner across different embodiments, and materials, features, processes, process steps, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

The devices, systems and methods described herein can comprise, consist essentially of, or consist of, the essential elements or features as well as optional elements or features described herein. "Consisting essentially of" means that the system, device, and/or method may include additional elements or features, but only if the additional elements or features do not materially alter the basic and novel characteristics of the claimed system, device, or method. As used in the description and the appended claims, the singular forms "a," "an," and "the" are intended to include the plural forms as well, unless the context clearly indicates otherwise.

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care product" means a product that regulates and/or improves a skin condition.

"Consumer skin care habits" refers to the skin care product use practices of a user (e.g., skin care routine or regimen). Some nonlimiting examples of consumer skin care habits include when a skin care product is used, how often skin care product is used, the order in which a set of skin care products are used, the amount of time associated with the use of the skin care products, the amount of skin care product used, and whether a user complies with the skin care product instructions.

Generally speaking, techniques for providing feedback regarding skin care products may be implemented in one or more skin care products, a skin care computing device, one or more other client computing devices, one or more network servers, and/or a system that includes several of these devices. However, for clarity, the examples below focus primarily on an embodiment in which a skin care computing device identifies a skin care product which is being used by a user, and determines product use event data for the skin care product, such as identification information for the skin care product such as the name of the skin care product, the date and/or time OF the use, the duration of the use, the manner in which the skin care product is used, other skin care products used in the same time frame as the skin care product, etc. The skin care computing device may then provide identification information for the user (e.g., a user ID, user login credentials, etc.) and the product use event data to a server device. The server device may then retrieve a user profile for the user based on the identification information and update the user profile to include the product use event data. In some scenarios, the skin care computing device may also provide user profile data to the server device, such as biographical information regarding the user, a current location of the user, an image of the user, or user preferences or goals regarding the skin care product. Accordingly, the server device may update the user profile with the user profile data.

The user profile may include skin care product use event data for the user at several time intervals, and the server device may analyze the skin care product use event data over time and/or the user profile data for the user to generate user feedback information. Then the server device provides the user feedback information to the skin care computing device which presents audio feedback via a speaker or visual feedback via a user interface. In other implementations, the skin care computing device forwards the user feedback information to a client computing device of the user for presentation on the client computing device, or the server device provides the user feedback information directly to the client computing device, for example via an SMS message, email, a push notification, etc.

FIG. 1 illustrates various aspects of an exemplary environment implementing a skin care system 100. The skin care system 100 includes a skin care computing device 102 which may be placed in a bathroom, such as on a bathroom sink. The skin care system 100 also includes one or more skin care products 104. The skin care computing device 102, described in more detail below, includes a voice assistant having one or several microphones 106, such as an array of microphones 106 and one or several speakers 108, such as an array of speakers 108. The voice assistant may also include processors and a memory storing instructions for receiving and analyzing voice input and providing voice output. The voice assistant included in the skin care computing device 102 may include the hardware and software components of the voice controlled assistant described in U.S. Pat. No. 9,304,736 filed on Apr. 18, 2013, incorporated by reference herein.

Additionally, the skin care computing device 102 include a user interface 110 for displaying information related to the skin care products, such as user feedback information regarding skin care products. The user interface 110 may also present user controls for the user to providing information about herself, such as identification information (e.g., user login credentials, a user ID, biographical information, user preferences or goals regarding skin care, etc. Moreover, the user interface 110 may include user controls for the user to provide information regarding the skin care products she uses, such as the names of the skin care products, how often she uses the skin care products, the manner in which she uses each skin care product, the duration of each use, etc.

Furthermore, the skin care computing device 102 may include a camera 112 for capturing video and/or images of the area within the field of view of the camera 112. In this manner, the skin care computing device 102 may identify skin care products 104 within an image or video frame to determine that a skin care product 104 is currently in use, determine the duration of the use, etc. The skin care computing device 102 may also include a communication interface (not shown) for connecting to a long-range communication network such as the Internet and for transmitting/receiving radio signals over a short-range communication network, such as NFC, Bluetooth, RFID, Wi-Fi, etc. For example, the skin care computing device 102 may include an RFID reader or an NFC reader to receive radio signals from RFID tags, NFC tags, Bluetooth Low Energy (BLE) tags, etc.

In some implementations, the skin care product 104 includes a radio identification tag (not shown), such as an RFID tag, NFC tag, BLE tag, etc., which transmits identification information for the skin care products to an RFID reader in the skin care computing device 102. In this manner, the skin care computing device 102 may identify a skin care product within a communication range of the skin care computing device 102, based on the radio identification tag, and may determine that the identified skin care product is being used by a user. The radio identification tag may be a passive radio identification tag, such that the radio identification tag does not include an internal power source such as a battery. Instead, the RFID or NFC reader within the communication range of the radio identification tag provides electromagnetic signals that energize the radio identification tag so that the radio identification tag can transmit a radio signal to the RFID or NFC reader which includes identification information for the skin care product 104. In other implementations, the skin care product 104 does not include a radio identification tag or any other transceiver, and the skin care computing device 102 may identify the skin care product 104 in other ways (e.g., identifying visual features within the skin care product 104 from images or video collected by the camera 112 which can be used to identify the skin care product 104, identifying labels, barcodes, or other text placed on the skin care product from the images or video, or obtaining an indication that the user is using the skin care product 104 via user controls on the user interface 110 or via the user's mobile device).

In some implementations, the skin care computing device 102 may include an environmental sensor for capturing environmental characteristics in the area surrounding the skin care computing device 102, such as the bathroom, the kitchen, the laundry room, the living room, etc. of the user's dwelling. The environmental sensor may be a temperature sensor, a humidity sensor, an acoustic sensor, an ultrasonic sensor, a radio antenna for example for receiving Wi-Fi or Bluetooth™ signals, a weighing scale, a wearable sensor, an air quality sensor such as a volatile organic compounds (VOC) sensor, or a depth sensor for generating a 3D point cloud of the area surrounding the environmental sensor, such as a light detection and ranging (LiDAR) sensor or an infrared (IR) sensor, each of which may be used in combination with the camera 112 to generate the 3D point cloud.

It may be particularly desirable to include an acoustic sensor (e.g., one or more microphones 106) for detecting audio characteristics such as the volume of sounds within the area, the frequency of the sounds within the area, the tone of the sounds within the area, and/or the directions in which the sounds came from within the area. In this manner, the skin care computing device 102 may identify activities being performed by the user based on the environmental sensor.

Figure 2:
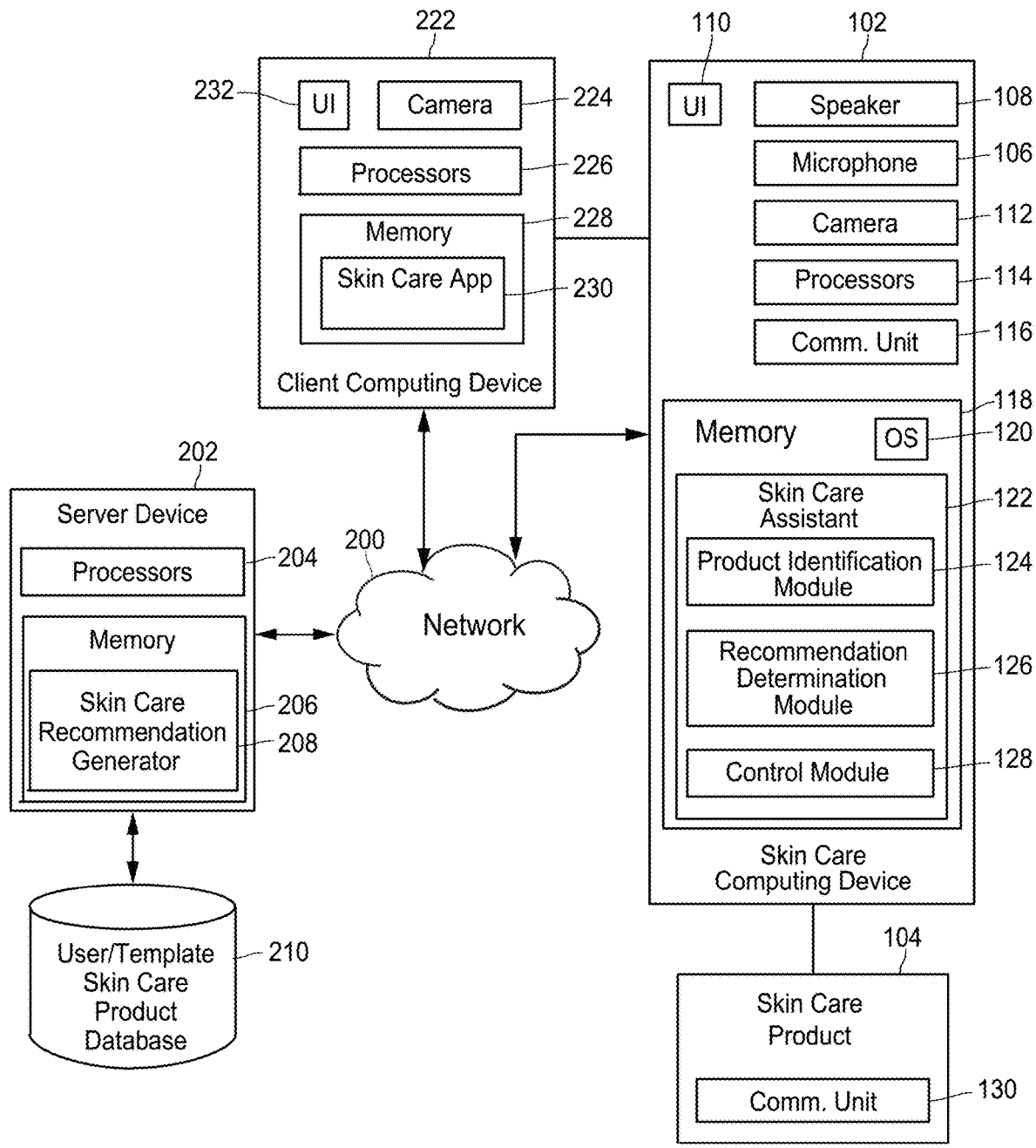
FIG. 2 illustrates an example of the system in which the skin care computing device can operate.

FIG. 2 illustrates an example communication system in which the skin care computing device 102 and the skin care product 104 can operate to enhance the user's experience with the skin care product. The skin care computing device 102 illustrated in FIG. 2 includes a user interface 110, a camera 112, one or more processors 114, a communication unit 116 to transmit and receive data over long-range and short-range communication networks, and a memory 118. The skin care computing device 102 has access to a wide area communication network 200 such as the Internet via a long-range wireless communication link (e.g., a cellular link). In the example configuration of FIG. 2, the skin care computing device 102 communicates with a server device 202 that generates user feedback information based on the user's interactions with their skin care products 104. The skin care computing device 102 may be configured to communicate with any number of suitable servers.

As described above, the skin care computing device 102 can also use a variety of arrangements, singly or in combination, to communicate with the user's skin care products 104. In some implementations, the skin care computing device 102 obtains identification information from the user's skin care products 104 via a short-range communication link, such as short-range radio frequency links including Bluetooth™, RFID, NFC, etc. Some skin care products 104 may include a communication component 130, such as an RFID tag, NFC tag, BLE tag, etc. Other skin care products 104 may not include the communication component 130. The skin care computing device 102 may also communicate with a client computing device 222 of the user such as a mobile device including a tablet or smartphone over a short-range communication link, such as short-range radio frequency links including Bluetooth™, WiFi (802.11 based or the like) or another type of radio frequency link, such as wireless USB.

The client computing device 222 may be a mobile device such as a tablet computer, a cell phone, a personal digital assistant (PDA), a smartphone, a laptop computer, a portable media player, a home phone, a pager, a wearable computing device, smart glasses, a smart watch or bracelet, a phablet, another smart device, etc. The client computing device 222 may also be a desktop computer. The client computing device 222 may include one or more processors 226, a non-transitory memory 228, a communication unit (not shown) to transmit and receive data via long-range and short-range communication networks, and a user interface 232 for presenting data to the user. The memory 228 may store, for example, instructions for a skin care application 230 that includes user controls for providing information regarding the user's skin care products, such as the names of the user's skin care products, the frequency, duration, and/or manner in which the user uses each skin care product, etc. The skin care application 230 may also include user controls for providing user profile data such as user login credentials, a user ID, the user's name or other biographical information, an image of the user such as a before and after picture, etc. Additionally, the skin care application 230 may receive user feedback information to present on the user interface 232 or as voice output via a speaker, The user feedback information may be received from the skin care computing device 102 via a short-range communication link, such as Bluetooth™ or from the server device 202 via a long-range communication link, such as the Internet or a cellular network.

The memory 118 can store instructions of the operating system 120 and a skin care assistant application 122. The skin care assistant application 122 may obtain an indication of a skin care product 104 being used, identify the skin care product 104 based on the indication, and generate and present user feedback information to the user to assist the user with the skin care product or related skin care products via a product identification module 124, a recommendation determination module 126, and a control module 128.

The skin care computing device 102 may obtain an indication of a skin care product 104 being used and the product identification module 124 may identify the skin care product 104 based on the obtained indication. The indication of the skin care product 104 may be provided with manual input via user controls on the user interface 110 of the skin care computing device 102. For example, the user may select the skin care product 104 from a list of skin care products included in a drop-down menu on the user interface 110. The product identification module 124 may then identify the selected skin care product 104 via the user controls. Additionally or alternatively, the indication of the skin care product 104 may be provided automatically, such as via a radio signal from the skin care product 104, an image or video of the skin care product 104, or environmental characteristics indicative of an activity performed by the user which is related to the skin care product 104, as described below. For example, the indication of the skin care product 104 may be dentification information from a radio identification tag. For example, the identification information may indicate that the skin care product 104 transmitting the radio signal is OLAY REGENERIST MICRO SCULPTING CREAM.

In some instances, the indication of the skin care product 104 may be an image or video of the area within the field of view of the camera 112. The camera 112 may periodically capture images or capture continuous video of the area in front of the camera 112, which may include a bathroom counter or an area where a user may sit in front of a bathroom mirror. Then within each image or video frame, the product identification module 124 may identify an object and determine a skin care product which corresponds to the object based on visual descriptors and semantic cues for the object. At least some of the visual descriptors and semantic cues for the object may be based on a product tag, a product label, a product color, a product shape, a product size, or a product logo. In some scenarios, an image or video frame may include multiple objects and the product identification module 124 may determine skin care products which correspond to each object. To identify objects within the image or video frame, the product identification module 124 may segment boundaries for the objects using edge detection, pixel entropy, or other image processing techniques. For example, when adjacent pixels in an image differ in intensity by more than a threshold amount, the product identification module 124 may identify the intersection between the adjacent pixels as a boundary of an object. In another example, when a cluster of pixels in the image differs in intensity by more than a threshold amount from an adjacent cluster of pixels, the product identification module 124 may identify the intersection between the adjacent pixels as a boundary of an object. In addition to performing the edge detection techniques described above to identify the boundaries of an object, the product identification module 124 may use an active contour model to refine the locations of the boundaries and further remove noise. Based on the boundary segmentation, the product identification module 124 may identify each of the objects in the image. For each identified object, the product identification module 124 may determine a size and shape of the object according to its boundaries.

In some instances, the product identification module 124 may also identify visual features within the object along with the corresponding locations of the visual features within the object. For example, a first visual feature may be located in the upper right corner of the object, a second visual feature may be located in the center of the object, etc. The visual feature may include a keypoint, which is a stable region within the object that is detectable regardless of blur, motion, distortion, orientation, illumination, scaling, and/or other changes in camera perspective. The stable regions may be extracted from the object using a scale-invariant feature transform (SIFT), speeded up robust features (SURF), fast retina keypoint (FREAK), binary robust invariant scalable keypoints (BRISK), or any other suitable computer vision techniques. In some embodiments, keypoints may be located at high-contrast regions of the object, such as edges within the object. A bounding box may be formed around a keypoint and the portion of the object created by the bounding box may be a visual feature. In some embodiments, each visual feature is encoded as a vector which may include attributes of the visual feature, such as RGB pixel values, the location of the visual feature within the object, etc.

Additionally, for each identified object, the product identification module 124 may identify semantic cues for the object, such as text displayed on the object (e.g., a product label), a tag on or adjacent to the object, a pattern or symbol on the object (e.g., a product logo), etc. To identify text with an object, the product identification module 124 may apply a stroke width transform (SWT). The SWT is used to find a portion of an image which includes text and filter out the remaining portions of the image which do not include text. In this manner, the text portion of the image may be converted to a text string. The SWT technique may be based on an assumption that all text characters in an image have the same stroke width. For example, when the letter 'T' is placed within an image, the pixel width of the horizontal line in the letter 'T' may be the same as the pixel width for the vertical line in the letter 'T' within the image. This width may also be the same for all other lines or curves that make up text characters within the image.

Based on this assumption, the product identification module 124 may identify text characters within an image by identifying several lines or curves having a same or similar width (e.g., within a threshold variance of each other). More specifically, the product identification module 124 may perform edge detection techniques within one of the objects, such as the edge detection techniques described above for boundary segmentation, to identify boundaries for lines and curves within the object. The product identification module 124 may then calculate pixel widths for each of these lines and curves based on the positions of their respective boundaries. When the pixel widths for several lines and/or curves are the same or are within a threshold variance of each other, the product identification module 124 may identify the lines and/or curves as text, and may filter out the remaining portions of the object.

Additional filtering steps may also be applied to identify the text characters within the image. For example, text characters may have minimum and maximum aspect ratios, such that the length of a text character does not exceed the width of the text character by more than a threshold amount. Accordingly, the identified lines and/or curves may be compared to minimum and maximum aspect ratios. If the length to width ratio of a candidate text character is outside the minimum or maximum aspect ratios, the candidate text character may be filtered out as a portion of the image which does not include text.

A threshold ratio between the diameter of a text character and the text character's average stroke width may also be used to filter out portions of the image which do not include text. For example, if the product identification module 124 identifies a portion of an image which resembles the letter 'O' the product identification module 124 may calculate the ratio of the diameter for the candidate text character to the average stroke width. When the ratio is less than the threshold ratio by more than a threshold variance (e.g., the candidate text character is donut-shaped) or the ratio is more than the threshold ratio by more than the threshold variance, the candidate text character may be filtered out as a portion of the image which does not include text. Moreover, the product identification module 124 may filter out candidate text characters having less than a minimum threshold size or greater than a maximum threshold size (e.g., a minimum height of 8 pixels and a maximum height of 300 pixels). In some embodiments, other filtering steps may also be applied such as filtering overlapping bounding boxes, or any other suitable filtering steps.

In addition to identifying text characters, the product identification module 124 may also use the SWT to identify words. For example, all text characters in a word may have the same color, may be spaced apart evenly, may be within a threshold distance from each other, and may be the same height or have height differences which are less than a threshold amount. Accordingly, the product identification module 124 may identify words by grouping identified text characters having the same color, that are within a threshold height difference of each other, that are within a threshold distance of each other, and/or that are spaced apart by the same distance.

In some embodiments, the product identification module 124 may use Maximally Stable Extremal Regions (MSER) techniques to identify text within an object or may use a combination of SWT and MSER to identify the text. Once text is identified within an object, the portion of the object containing text may be provided to an optical character recognition (OCR) engine which may convert an image (e.g., the portion of the object containing text) to a text string. In some embodiments, for each identified object, the product identification module 124 may identify a barcode or QR code within the identified object and may decode the barcode or QR code converting the barcode or QR code to a text string or other data stream which may be used as a semantic cue.

To identify a skin care product which corresponds to an object, the product identification module 124 may compare each of the visual features, semantic cues, and/or other visual characteristics for the object to visual descriptors, semantic cues, and/or other visual characteristics for templates of skin care products to determine a likelihood that the object corresponds to one of the skin care products. The skin care computing device 102 may store the templates of skin care products in a database. Each template may include the visual features, semantic cues, and/or other visual characteristics for the template skin care product. For example, each identified text string for an object may be compared to text strings in the templates of skin care products to determine likelihoods that the object corresponds to each template skin care product. The skin care product having the highest likelihood for the object or having a likelihood that exceeds a likelihood threshold may be identified as the skin care product corresponding to the object.

In some embodiments, the product identification module 124 may generate a machine learning model for identifying skin care products based on visual features and semantic cues using image classification and/or machine learning techniques. The machine learning techniques may include linear regression, polynomial regression, logistic regression, random forests, boosting, nearest neighbors, Bayesian networks, neural networks, deep learning, support vector machines, or any other suitable machine learning technique. Then the product identification module 124 may apply the visual features and semantic cues for the object to the machine learning model to identify the skin care product corresponding to the object.

In some embodiments, the template features and template semantic cues may be compared to the features and semantic cues for an object using a nearest neighbors algorithm that creates numerical representations of the features and semantic cues to generate feature vectors (e.g., a pixel width and height of a skin care product) and RGB pixel values for the skin care product. The numerical representations of the features or feature vectors of the object may be compared to the feature vectors of template skin care products (e.g., stored in a database) to determine a vector distance between the features of the object and each template skin care product.

In some instances, a semantic cue may be compared to text in the template skin care products to identify the amount of matching text characters, words, or symbols to determine a vector distance between the semantic cues of the object and each template skin care product. The product identification module 124 may generate vector distances for each vector (e.g., each visual feature and semantic cue) and combine the individual vector distances to generate an overall vector distance between the object and a particular template skin care product. The product identification module 124 may then identify the skin care product which corresponds to the object based on the amount of similarity, or the vector distance in the nearest neighbors algorithm, between the visual features and semantic cues for the object and the visual features and semantic cues for the template skin care products. The product identification module 124 may identify the template skin care product having the smallest overall vector distance between the object and the template skin care product as the template skin care product corresponding to the object.

In other examples, the product identification module 124 may provide images or video of the area within the field of view of the camera 112 to the server device 202 which may identify an object and determine a skin care product which corresponds to the object using similar techniques as described above. Then the server device 202 may provide the identified skin care products to the product identification module 124. In any event, in addition to identifying a skin care product 104 being used by a user, the product identification module 124 may identify consumer habits, such as product use event data for the skin care product 104. The product use event data may include identification information for the skin care product 104 such as the name of the skin care product, the date and/or time of the use, the duration of the use, the manner in which the skin care product 104 is used, other skin care products used in the same time frame as the skin care product 104, etc.

The product identification module 124 may determine the date and/or time of the use based on the date and/or time when the product identification module 124 identifies the skin care product 104. For example, when the skin care computing device 102 receives identification information from a radio identification tag provided by the skin care product 104, the product identification module 124 may record the date and/or time in which the identification information is received.

Additionally, the product identification module 124 may determine the duration of the use by determining when the skin care product 104 can no longer be identified. For example, the product identification module 124 may record the amount of time until the skin care computing device 102 stops receiving a radio signal from the skin care product 104, until the skin care product 104 is no longer within the field of view of the camera 112, etc.

Furthermore, the product identification module 124 may identify other skin care products used in the same time frame as the skin care product 104 by identifying the other skin care products in a similar manner as described above, and comparing identification times for each of the other skin care products to the identification time for the skin care product. If another skin care product is identified within a threshold time period (e.g., 2 minutes, 5 minutes, 10 minutes, etc.) of the skin care product, the product identification module 124 may determine that the other skin care product was used in the same time frame as the skin care product 104. For example, the product identification module 124 may determine that 5 skin care products were used within a ten minute time period, and thus may determine that each of the 5 skin care products was used in the same time frame. The product identification module 124 may also generate an order in which a set of skin care products were used when the set of skin care products were used in the same time frame.

Moreover, to determine the manner in which the skin care product 104 is used, the skin care computing device 102 may present questions on the user interface 110 or via the speaker 108 which are related to the use of the identified skin care product 104. Accordingly, the user may respond to the questions with voice responses which are received via the microphone or via user controls on the user interface 110, such as drop-down menus, text fields, etc. For example, when the skin care product 104 is eye makeup, the skin care computing device 102 may ask which color is being used, where the eye makeup is being applied around the eye, etc. In some implementations, the product identification module 124 may determine the manner in which the skin care product 104 is being used based on the user's responses to the questions. In other implementations, the product identification module 124 may determine the manner in which the skin care product 104 is being used by analyzing the images or video from the camera 112 using computer vision techniques. For example, the product identification module 124 may identify the user's face and facial features from the images such as the user's eyes, lips, and nose, and may determine where the user is applying makeup, lipstick, moisturizer, etc., on her face.

The product identification module 124 may be configured to identify a user. For example, the product identification module 124 may obtain an indication of the identity of the user from manual input via user controls on the user interface 110 of the skin care computing device 102. In some instances, a user may login to a user profile using login credentials (e.g., name, password, or other suitable identification information). Additionally or alternatively, the product identification module 124 may obtain the indication of the identity of the user automatically from environmental sensor data, such as an image or video of the user and/or vocal data from the user.

The skin care computing device 102 may store template images of each of each user who utilize the skin care computing device 102. For example, the skin care computing device 102 may store images, video, facial feature patterns, fingerprints, voice recordings, audio signatures, and/or other biometric data for each user. The product identification module 124 may compare the environmental sensor data to the stored biometric data using conventional computer-based methods (e.g., machine learning techniques) to identify the user. Some nonlimiting examples of machine learning techniques include linear regression, polynomial regression, logistic regression, random forests, boosting, nearest neighbors, Bayesian networks, neural networks, deep learning, support vector machines, combinations of these and the like. In some embodiments, the template facial features and/or template voice features may be compared to the facial features and/or voice features for a user whose identity is unknown using, for example a nearest neighbors algorithm to obtain an identifier (e.g., user ID) for the unknown user.

The recommendation determination module 126 may provide product use event data for the identified skin care product 104 and/or activity data for the activity as well as identification information for the user (e.g., user login credentials, a user ID, etc.) to the server device 202. The server device 202 may store the activity data and/or the product use event data in a user profile for the user, which may include historical product use event data for the identified skin care product 104 and for other skin care products and/or historical activity data for the identified activities and for other activities. The user profile may also include user profile data for the user, such as biographical information regarding the user, a current location of the user, an image of the user, or user preferences or goals regarding the skin care product. In some implementations, the skin care computing device 102 or the user's client computing device 222 obtains user profile data from the user and provides the user profile data to the server device 202. For example, the user's client computing device 222 may provide location data (e.g., obtained via a positioning sensor such as a GPS module or via an IP address), to the server device 202 which may be the user's current location. The server device 202 may then store the user profile data in the user profile for the user.

Example data tables 300, 400 illustrating user profile data and product use event data are illustrated in FIGS. 3 and 4, respectively. As shown in the data table 300 of FIG. 3, user profile data in a user profile may include a user ID 302, a name of the user 304, an address of the user 306, a date of birth of the user 308, skin care goals provided by the user 310, reported cosmetic issues provided by the user 312, rewards points for the user 314, or any other suitable information about the user. The data table 300 may also include images of the user (not shown), user performance metrics related to product usage (not shown), etc. As shown in the data table 400 of FIG. 4, product use event data in a user profile may include a user ID 402 which may be the same user ID as in the user profile data for associating the product use event data with the user. The product use event data may also include the name of the skin care product 404, the date and/or time of the use 406, the duration of the use 408, and the manner of use 410 describing how the skin care product was used. For example, as indicated in the data table 400, Jane Smith (User ID 2) applied Olay™ Total Effects Whip Face Moisturizer on Jul. 26, 2019 at 9:14 a.m. for 1 minute. She rubbed the moisturizer unevenly on parts of her face. Back on July 14, Jane Smith applied the Olay™ Total Effects Whip Face Moisturizer at 7:15 p.m. for 30 seconds. That time she rubbed the moisturizer evenly on her entire face. Additionally, on July 22, Jane Smith used a SK-II™ Facial Treatment Mask at 9:37 a.m. for 7 minutes. She placed the mask on her face, left it there for 7 minutes, and rinsed it off.

The server device 202 may include one or more processors 204, a communication unit (not shown) to transmit and receive data over long-range and short-range communication networks, and a memory 206. The server device 202 may also store a data table (not shown) which includes activity data. Activity data in a user profile may include a user ID which may be the same user ID as in the user profile data for associating the activity data with the user. The activity data may also include the type of the activity, the date and/or time of the activity, and the duration of the activity. Furthermore, the activity data may include the frequency of the activity over a particular time period (e.g., a day, a week, a month) based on the dates and/or times of the activity and/or other metrics based on the activity data. The server device 202 may analyze the product use event data for a particular skin care product, the activity data for a particular type of activity, and/or the user profile data for the user to generate user feedback information to assist the user in using the skin care product or related skin care products. This may enhance the user's experience with the skin care products and provide improved results from using the skin care products.

The memory 206 can store instructions of an operating system (not shown) and a skin care recommendation generator 208. The server device 202 may also be communicatively coupled to a database 210 that stores user profiles for several users, where each user profile includes user profile data and product use event data as described above. The database 210 may also store templates of skin care products including visual features, semantic cues, and/or other visual characteristics for the template skin care products. Moreover, the database 210 may store audio signatures for various activities each including a set of audio characteristics which correspond to the activity. Additionally, the database 210 may store machine learning models generated based on the visual features, semantic cues, and/or other visual characteristics of the template skin care products and/or based on the audio signatures for the various activities. Furthermore, for each skin care product or for each type of skin care product, the database 210 may store a set of rules regarding the appropriate frequency, duration, and manner of use for the skin care product. The rules may differ depending on the demographics of a particular user. For example, the rules may indicate that users in a first age group should moisturize more often than users in a second age group. In addition to sets of rules, the database 210 may store machine learning models for determining the appropriate frequency, duration, and manner of use for the skin care product that is specific to a particular user based on the user's previous patterns of use and/or the results experienced by the user. For example, if a general rule is to moisturize daily, but the user's product use event data indicates that the user has been moisturizing weekly yet recent images of the user indicates that her skin texture has greatly improved, a user-specific machine learning model may be adjusted such that the appropriate moisturizing frequency for the user is weekly.

Still further, the database 210 may store a set of rules regarding the appropriate frequency, duration, and manner of use for a particular activity. The set of rules may also include an estimated total number of times the activity may be performed and/or an estimated total duration over multiple instances of performing the activity before products related to the activity need to be replenished, such as the number of showers before the user needs to replace the soap and shampoo. In addition to sets of rules, the database 210 may store machine learning models for determining the appropriate frequency, duration, and manner of use for the particular activity that is specific to a particular user based on the user's previous patterns of use and/or the results experienced by the user.

The skin care recommendation generator 208 may analyze the activity data and/or the product use event data at several instances in time for the identified skin care product 104 (e.g., from the user profile in the database 210) to generate the user feedback information. For example, the skin care recommendation generator 208 may analyze the activity data and/or the product use event data over a particular time window (e.g., the previous year, the previous month, the previous week, etc.). Then the skin care recommendation generator 208 may determine product use metrics for the skin care product 104 such as a frequency of use over the particular time window, an average duration of use, the time of day of the use, etc. For example, for the Olay™ Total Effects Whip Face Moisturizer described in FIG. 4, the skin care recommendation generator 208 may determine that the user applied the moisturizer about once a week. The skin care recommendation generator 208 may also determine activity metrics for the activity such as a frequency of the activity over the particular time window, an average duration of the activity, the time of day of the activity, etc.

The skin care recommendation generator 208 may compare the product use metrics and/or the product use event data to the set of rules for the identified skin care product 104, for example, from the database 210 to generate the user feedback information. The skin care recommendation generator 208 may also compare the activity metrics and/or activity data to the set of rules for the identified activity, for example from the database 210 to generate the user feedback information. The activity metrics, activity data, product use metrics, and/or the product use event data may be compared to the set of rules in view of the user profile data for the user, such as demographics, or the user's skin care goals and reported issues.

In other implementations, the skin care recommendation generator 208 may apply the activity metrics, activity data, product use metrics, product use event data, and/or user profile data to a machine learning model generated based on the performances of other users. For example, the skin care recommendation generator 208 may train the machine learning model using on a first set of activity metrics, activity data, product use metrics, product use event data, and/or user profile data for a first set of users who improved their cosmetic deficiencies with the skin care product and a second set of activity metrics, activity data, product use metrics, product use event data, and/or user profile data for a second set of users who did not improve their cosmetic deficiencies with the skin care product. For each type of user feedback information (e.g., rewards, recommendations, advice, etc.), the skin care recommendation generator 208 may train the machine learning model using a first set of activity metrics, activity data, product use metrics, product use event data, and/or user profile data for a first set of users who received the type of user feedback information for the skin care product and a second set of activity metrics, activity data, product use metrics, product use event data, and/or user profile data for a second set of users who did not receive the type of user feedback information for the skin care product.

The skin care recommendation generator 208 may generate user feedback information using the set of rules and/or the machine learning models. The user feedback information may include a recommendation to replenish the skin care product (e.g., after a threshold number of uses of the skin care product which in some instances may be determined via the activity data, or when the skin care product exceeds a threshold age according to the set of rules and/or the machine learning models). The user feedback information may include advice on how to use the skin care product or a recommendation on how to improve the use of the skin care product.

For each skin care product, the server device 202 may store a set of instructions on using the skin care product, for example, in the database 210. When the user is using the skin care product incorrectly based on product use event data, the skin care recommendation generator 208 may generate advice on how to use the skin care product. For example, as described above with reference to FIG. 4, the user placed a SK-II™ Facial Treatment Mask on their face, left it there for 7 minutes, and rinsed it off. The set of rules for the SK-II™ Facial Treatment Mask may indicate that the user should not rinse off the mask and instead rub it in. Accordingly, the skin care recommendation generator 208 may generate advice indicating that next time the user should rub in the mask without rinsing it off. The advice may also include the frequency and duration in which to use the skin care product and/or a description of the frequency and duration in which the user is using the skin care product. The skin care recommendation generator 208 may generate advice indicating the frequency and/or duration when the user first uses the skin care product according to the product use event data or when the user is using the skin care product too frequently, not frequently enough, for too long, or for not long enough according to the product use event data and the set of instructions on using the skin care product.

The advice on how to use the product may be based on the consumer habits for the user. For example, if the user's habits deviate from the set of rules for using a particular product, the skin care recommendation generator 208 may generate advice indicating how to use the product. Still further, the user feedback information may include opportunities for optimizing a particular hygiene regimen based on the user's habits. More specifically, the user feedback information may include a particular order in which the user should use a set of products for a particular hygiene regimen, such as when the user's habits indicate that the user does not follow the particular order. For example, when the user's habits indicate that the user applies concealer before putting on foundation, the user feedback information may include a recommendation to apply the concealer after putting on foundation. Additionally, the user feedback information may include recommendations for additional or alternative products to use during the particular hygiene regimen along with the products the user is currently using in the regimen.

In some embodiments, the advice on how to use the product may be based on user profile data such as the weather conditions at the user's location, the time of year, or the time of day. If it is a hot, humid day or it is raining, the skin care recommendation generator 208 may recommend different types of use of skin care products than on a sunny day with low humidity. Also, if it is the daytime during the summer, the skin care recommendation generator 208 may recommend purchasing a daytime moisturizer with sunscreen to go along with the user's nighttime moisturizer. In the winter, the skin care recommendation generator 208 may recommend that the user apply the same moisturizer during the day and at night.

In some instances, the user feedback information may include recommendations to purchase related skin care products. For example, the server device 202 may store lists of skin care products which work well together according to their ingredients or the effects of the skin care products on other users. When the user is using a particular type of shampoo, the skin care recommendation generator 208 may recommend a particular type of conditioner that compliments the shampoo. The user profile may indicate that the user in the past used a particular skin care product within the same time frame as another skin care product. The skin care recommendation generator 208 may recommend that the user once again purchase the particular care product to use with the other skin care product.

The user feedback information may include a user performance metric such as a score based on the duration and/or frequency in which the user uses a particular skin care product. For example, the user performance metric may be a score from 0-100 which increases each time the user uses conditioner. If the user does not use conditioner for a threshold time period, the score may decrease or reset to 0. In some implementations, the skin care recommendation generator 208 generates the user performance metric using a machine learning model, such as a regression model. As described above, the machine learning model may be trained using on a first set of activity metrics, activity data, product use metrics and/or product use event data for a first set of users who improved their cosmetic deficiencies with the skin care product and a second set of activity metrics, activity data, product use metrics and/or product use event data for a second set of users who did not improve their cosmetic deficiencies with the skin care product. Then the skin care recommendation generator 208 may apply the user's activity metric, activity data, product use metric, and/or product use event data to the machine learning model to generate the user performance metric.

The user feedback information may also include rewards which may be provided when a user performance metric exceeds a threshold value, when the user uses more than a threshold number of different skin care products, when the user follows recommendations or advice provided by the skin care computing device. The user performance metric may also be a comparison to the performances of other users. In some embodiments, the skin care recommendation generator 208 may compare the user's performance to the performances of other users in the same demographic (e.g., age group). For example, the user may have a raw user performance metric for eye makeup of 65 but this may be in the 75$^{th}$ percentile of raw user performance metrics compared to other users in the same age group, same geographic area, etc. Accordingly, the user feedback information may provide a raw user performance metric, a percentile or ranking of the raw user performance metric relative to other users, an adjusted user performance metric factoring in the user's performance relative to other users, or any other suitable relative user performance metric. In some instances, the user feedback information may include recommendations on how to improve a user performance metric, encouragement to continue using the skin care product to reach a high score and receive rewards points or other incentives for maintaining consistent use of the skin care product.

Example user feedback information is illustrated in the data table 500 of FIG. 5. For example, the skin care recommendation generator 208 may recommend that the user "Use a skin care product with sunscreen to protect against harmful UV rays." For moisturizer, the skin care recommendation generator 208 may advise, "In the past month, you have been moisturizing about twice a week. Make sure you moisturize everyday." In another example, the skin care recommendation generator 208 may advise, "Don't forget to replace your skin care product after 5 uses." In yet another example, the skin care recommendation generator 208 may recommend that the user "Buy OLAY Wrinkle Repair Serum to use along with your moisturizer. Another example of user feedback information may be, "You have earned 200 rewards points for maintaining proper skin care habits."

The database 210 may also store previous user feedback information provided to the user, so that the skin care computing device 102 does not repeatedly provide the user with the same user feedback information. Based on the user's response to various user feedback information the skin care recommendation generator 208 may learn which types of user feedback information improve the user's performance. For example, the skin care recommendation generator 208 may learn that the user does not purchase recommended related products, and thus may stop providing related products recommendations. The skin care recommendation generator 208 may provide the user feedback information to the skin care computing device 102, or the client computing device 222 via an SMS message, email, push notification, etc. In other implementations, the recommendation determination module 126 in the skin care computing device 102 may analyze the product use event data for the user to generate the user feedback information without sending the product use event data to the server device 202.

The control module 128 may control operation of the skin care computing device 102 by for example, presenting a display which includes the user feedback information via the user interface 110, presenting audio output which includes the user feedback information via the speaker 108, providing haptic feedback indicative of the user feedback information via a vibration motor, or transmitting the user feedback information to the client computing device 222 via the communication unit 116.

Figure 6:
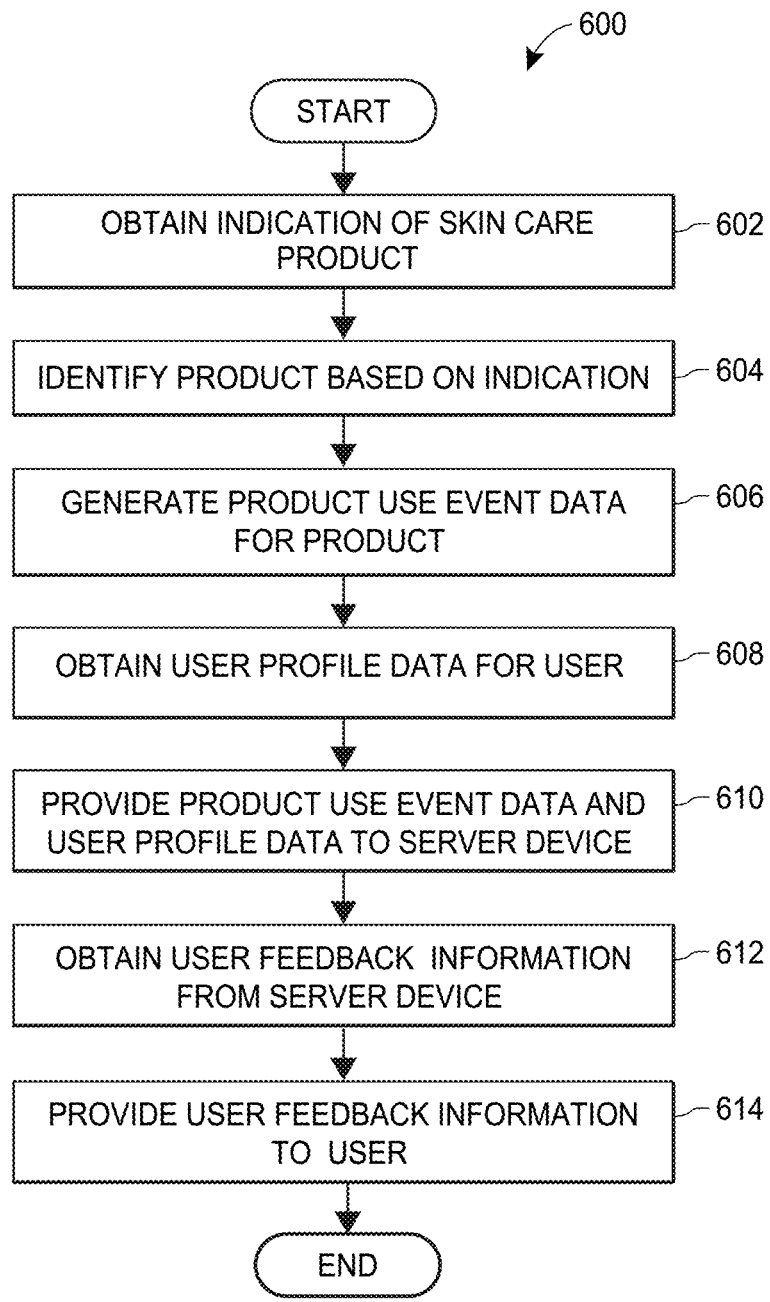
FIG. 6 is a flow diagram illustrating an example of the present method.

FIG. 6 illustrates a flow diagram representing an example method 600 for providing feedback regarding skin care products. The method 600 may be performed by the skin care assistant application 122 and executed on the skin care computing device 102. In some embodiments, the method 600 may be implemented in a set of instructions stored on a non-transitory computer-readable memory and executable on one or more processors of the skin care computing device 102. For example, the method 600 may be at least partially performed by the product identification module 124, the recommendation determination module 126, and the control module 128, as shown in FIG. 2.

At block 602, an indication of a skin care product 104 being used by a user is obtained. The indication of the skin care product 104 may be provided with manual input via user controls on the user interface 110 of the skin care computing device 102 or the client computing device 222. For example, the user may select the skin care product 104 from a list of skin care products included in a drop-down menu on the user interface 110. The indication of the skin care product 104 may also be provided automatically, such as via a radio signal from the skin care product 104, or an image or video of the skin care product 104.

In some embodiments, an indication of an activity may be obtained. The indication of the activity may be provided automatically, such as via environmental characteristics for the area surrounding the skin care computing device 102 detected by an environmental sensor, which may be any one of, any two of, or any suitable combination of an audio sensor such as a microphone or an array of microphones, a temperature sensor, an ultrasonic sensor, a radio antenna for example for receiving Wi-Fi or Bluetooth signals, a weighing scale, a wearable sensor, an air quality sensor such as a VOC sensor, a depth sensor for generating a 3D point cloud of the area surrounding the environmental sensor, such as a LiDAR sensor or an IR sensor, and/or a humidity sensor.

At block 604, the skin care product 104 is identified based on the obtained indication. In the case of manual input, the skin care computing device 102 may identify the selected skin care product 104 via the user controls. When the indication of the skin care product 104 is a radio signal, the skin care computing device 102 may identify the skin care product 104 transmitting the radio signal based on the identification information included in the radio signal. Furthermore, when the indication of the skin care product 104 is an image or video, the skin care computing device 102 may identify the skin care product 104 by analyzing images or video frames using the computer vision techniques described above to identify an object within the images or video frames and identify visual features, semantic cues, and/or other visual characteristics for the object. Then the skin care computing device 102 may compare the visual features, semantic cues, and/or other visual characteristics to visual features, semantic cues, and/or other visual characteristics for templates of skin care products to determine a likelihood that the object corresponds to one of the skin care products. In other implementations, the skin care computing device 102 or the server device 202 may generate a machine learning model for identifying skin care products based on visual features and semantic cues using image classification and/or machine learning techniques. Then the skin care computing device 102 may apply the visual features and semantic cues for the object to the machine learning model to identify the skin care product corresponding to the object.

In some instances, the skin care computing device 102 may provide the obtained indication of the skin care product 104 to the server device 202 to identify the skin care product 104 corresponding to the indication. Then the server device 202 provides the identified skin care product 104 and/or the identified activity to the skin care computing device 102. In addition to identifying the skin care product 104, the skin care computing device 102 may identify product use event data for the skin care product 104 based on the user's interaction with the skin care product 104 (block 606). The product use event data may include identification information for the skin care product 104 such as the name of the skin care product, the date and/or time of the use, the duration of the use, the manner in which the skin care product 104 is used, other skin care products used in the same time frame as the skin care product 104. For example, when the skin care computing device 102 receives identification information from a radio identification tag provided by the skin care product 104, the skin care computing device 102 may record the date and/or time in which the identification information is received. The skin care computing device 102 may determine the duration of the use by determining when the skin care product 104 can no longer be identified. Furthermore, the skin care computing device 102 may identify other skin care products used in the same time frame as the skin care product 104 by identifying the other skin care products in a similar manner as described above, and comparing identification times for each of the other skin care products to the identification time for the skin care product.

Moreover, to determine the manner in which the skin care product 104 is used, the skin care computing device 102 may present questions on the user interface 110 or via the speaker 108 which are related to the use of the identified skin care product 104. Accordingly, the user may respond to the questions with voice responses which are received via the microphone or via user controls on the user interface 110, such as drop-down menus, text fields, etc. In other implementations, the skin care computing device 102 may determine the manner in which the skin care product 104 is being used by analyzing the images or video from the camera 112 using computer vision techniques. For example, the skin care computing device 102 may identify the user's face and facial features from the images such as the user's eyes, lips, and nose, and may determine where the user is applying makeup, lipstick, moisturizer, etc., on her face. In yet other implementations, the skin care computing device 102 may determine the manner in which the skin care product 104 is being used based on the activity data. More specifically, the activity data may indicate the type of activity the user performed while using the skin care product 104. It may also be desirable for the skin care computing device 102 to identify activity data such as the type of activity, the date and/or time of the activity, and/or the duration of the activity.

In some embodiments, the skin care computing device 102 or the client computing device 222 also obtains user profile data for the user, such as biographical and/or biometric information regarding the user, a current location of the user, an image of the user, or user preferences or goals regarding the skin care product. Then the skin care computing device 102 or the client computing device 222 provides the user profile data to the server device 202.

At block 608, the skin care computing device 102 provides the activity data, the product use event data for the identified skin care product 104, and/or identification information for the user (e.g., user login credentials, a user ID, etc.) to the server device 202. The server device 202 may analyze the activity data for the identified activity, the product use event data for the identified skin care product 104, and/or the user profile data for the user to generate user feedback information to assist the user in using the skin care product or related skin care products. More specifically, the server device 202 may analyze the activity data and/or the product use event data at several instances in time for the identified skin care product 104 and/or identified activity to generate the user feedback information. For example, the server device 202 may analyze the activity data and/or the product use event data over a particular time window (e.g., the previous year, the previous month, the previous week, etc.). Then the server device 202 may determine product use metrics for the skin care product 104 such as a frequency of use over the particular time window, an average duration of use, the time of day of the use, etc. The server device 202 may also identify activity metrics based on the activity data, such as a frequency of the activity over the particular time window, an average duration of the activity, the time of day of the activity, etc. The server device 202 may then compare the activity data, the activity metrics, the product use metrics and/or the product use event data to a set of rules for the identified skin care product 104, for example from the database 210 to generate the user feedback information. In other implementations, the server device 202 may apply the activity data, the activity metrics, the product use metrics, product use event data, and/or user profile data to a machine learning model generated based on the performances of other users.

The server device 202 may generate several types of user feedback information. The database 210 may also store previous user feedback information provided to the user, and the server device 202 may provide types of user feedback information to the skin care computing device 102 or the client computing device 222 which have not been presented to the user within a threshold time period. In other implementations, some types of user feedback information may be provided more often than others, such as user performance metrics. The server device 202 may provide an updated user performance metric to the user each time the user performance metric changes. On the other hand, the server device 202 may only provide recommendations on how to use the skin care product once a week or once a month, for example.

At block 612, the skin care computing device 102 obtains the user feedback information from the server device 202. In other implementations, the skin care computing device 102 generates the user feedback information based on the activity data, the product use event data for the skin care product, and/or the user profile data. In any event, the skin care computing device 102 presents the user feedback information to the user (block 614). The skin care computing device 102 may present a display on the user interface 110 that includes the user feedback information, may provide haptic feedback via a vibration motor indicative of the user feedback information, may turn a set of light emitting diodes (LEDs) on or off based on the user feedback information, may present voice output which includes the user feedback information via the speaker 108, or may transmit the user feedback information for display on the client computing device 222 via the communication unit 116.

Figure 7:
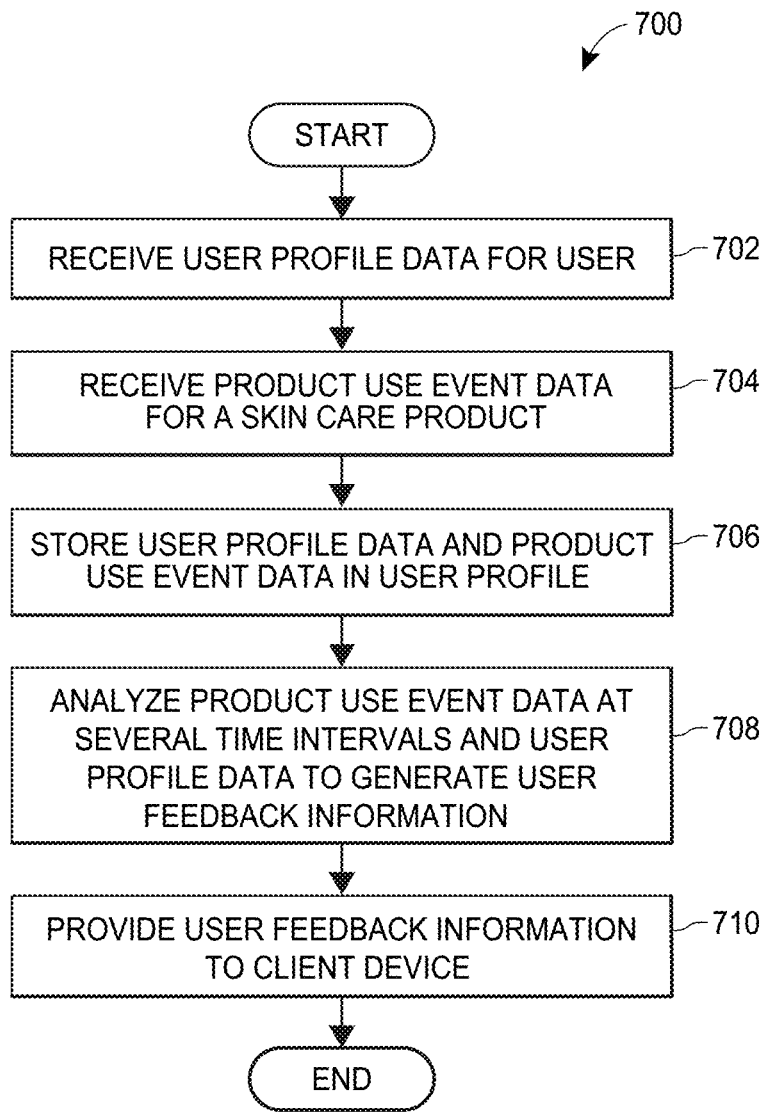
FIG. 7 is a flow diagram illustrating an example of the present method.

FIG. 7 illustrates a flow diagram representing an example method 700 for generating the feedback regarding skin care products. The method 700 may be performed by the server device 202. In some embodiments, the method 700 may be implemented in a set of instructions stored on a non-transitory computer-readable memory and executable on one or more processors of the server device 202. For example, the method 700 may be at least partially performed by the skin care recommendation generator 208, as shown in FIG. 2.

At block 702, the server device 202 receives user profile data for a user. The server device 202 may receive the user profile data from the user's skin care computing device 102 or client computing device 222. The user profile data may include biographical and/or biometric information regarding the user (e.g., a current location of the user, an image of the user, or user preferences or goals regarding the skin care product). In some implementations, the server device 202 stores a user profile for the user in a database 210 which includes at least some of the user profile data. The server device 202 may then update the user profile with user profile data received from the skin care computing device 102 or client computing device 222.

The server device 202 also receives product use event data indicative of the user's interaction with a skin care product 104 (block 704). For example, each time the skin care computing device 102 or the client computing device 222 identifies that the user is interacting with a skin care product 104, the skin care computing device 102 or the client computing device 222 may generate a record of the use and provide the generated record to the server device 202. This may include identification information for the skin care product 104 such as the name of the skin care product, the date and/or time of the use, the duration of the use, the manner in which the skin care product 104 is used, other skin care products used in the same time frame as the skin care product 104, etc.

Additionally, the server device 202 may receive activity data indicative of an activity performed by the user. For example, each time the skin care computing device 102 identifies an activity, the skin care computing device 102 may generate a record of the activity and provide the generated record to the server device 202. This may include activity data, such as the type of activity, the duration of the activity, the date and/or time of the activity, one or more skin care products related to the activity, etc.

The server device 202 may store the activity data, the product use event data, and/or the user profile data in the user profile for the user, for example, in the database 210 (block 706). In some embodiments, each time the server device 202 receives a new instance of activity data and/or product use event data, the server device 202 analyzes the new instance of activity data and/or product use event data and previously stored instances of activity data and/or product use event data for the activity/skin care product to generate user feedback information (block 708). For example, the server device 202 may analyze the activity data and/or product use event data over a particular time window (e.g., the previous year, the previous month, the previous week, etc.), which may include several instances of activity data and/or product use event data at different time intervals for the same activity and/or skin care product 104.

The server device 202 may determine product use metrics for the skin care product 104, such as a frequency of use over the particular time window, an average duration of use, and/or the time of day of the use. The server device 202 may also determine activity metrics for the activity such as a frequency of the activity over the particular time window, an average duration of the activity, and/or the time of day of the activity. The server device 202 may then compare the activity data, activity metrics, product use metrics, and/or the product use event data to a set of rules for the identified skin care product 104 and/or the identified activity, for example from the database 210 to generate the user feedback information. In other implementations, the server device 202 may apply the activity data, activity metrics, product use metrics, product use event data, and/or user profile data to a machine learning model generated based on the performances of other users.

The user feedback information may include a recommendation to replenish the skin care product, advice on how to use the skin care product, a recommendation on how to improve the use of the skin care product, the frequency and/or duration in which to use the skin care product, a description of the frequency and/or duration in which the user is using the skin care product, a recommendation to purchase a related skin care product, a user performance metric, a recommendation on how to improve a user performance metric, encouragement to continue using the skin care product, and/or incentives for maintaining consistent use of the skin care product (e.g., reach a higher score and/or receive reward points). In some instances, the user feedback information may also include rewards for when a user performance metric exceeds a threshold value, when the user uses more than a threshold number of different skin care products, and/or when the user follows recommendations or advice provided by the skin care computing device.

The user performance metric may be a skin care product-specific user performance metric, such that the server device 202 generates a different user performance metric for each of several skin care products or each of several types of skin care product. In some instances, the user performance metric may be a score, such as a point value of 0 to 100, which increases or decreases based on the duration and/or frequency in which the user uses a particular skin care product. Each user performance metric may also be a comparison to the performances of other users. In some embodiments, the server device 202 may compare the user's performance to the performances of other users in the same demographic (e.g., age group). For example, the user may have a raw user performance metric for eye makeup of 65 but this may be in the $75^{th}$ percentile of raw user performance metrics compared to other users in the same age group, same geographic area, etc. Accordingly, the server device 202 may generate a raw user performance metric, an adjusted user performance metric factoring in the user's performance relative to other users, and/or a percentile or ranking of the raw user performance metric relative to other users for the same skin care product.

The database 210 may store previous user feedback information provided to the user, so that the skin care computing device 102 does not repeatedly provide the user with the same user feedback information. Based on the user's response to various user feedback information the server device 202 may learn which types of user feedback information improve the user's performance. For example, the server device 202 may learn that the user does not purchase recommended related products, and thus may stop providing related products recommendations.

At block 710, the server device 202 may provide the user feedback information to a client device, such as skin care computing device 102, or the client computing device 222 via an SMS message, email, push notification, etc.

It is to be appreciated that certain features of the devices and methods herein are described herein as including logic or a number of routines, subroutines, applications, or instructions. These may constitute either software (e.g., code embodied on a machine-readable medium or in a transmission signal) or hardware. In hardware, the routines, subroutines, applications, or instructions are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, i.e., an element or device that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules. Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of the operations may be distributed among the one or more processors residing in one or more computers. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information. Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A computing device for providing feedback regarding skin care products, the computing device comprising:
   a user interface;
   a communication interface;
   one or more processors; and
   a non-transitory computer-readable memory coupled to the one or more processors, the user interface, and the communication interface, wherein the non-transitory computer-readable memory comprises stored instructions that, when executed by the one or more processors, cause the computing device to:
      obtain an indication of product usage of a skin care product by a user;
      identify the skin care product based on the obtained indication of product usage;
      obtain product use event data associated with the user for the skin care product, the product use event data comprises one or more of the following: a time in which the user used the skin care product, a date in which the user used the skin care product, an order in which the user used the skin care product relative to other skin care products, indications of the other skin care products used with the skin care product, a duration in which the user used the skin care product, a manner in which the user used the skin care product, or a combination thereof;
      obtain user profile data for a user profile of the user;
      generate a machine learning model for identifying skin care products; wherein the machine learning model is trained using a first set of activity metrics, activity data, product use metrics and product use event data for a first set of users who improved their cosmetic deficiencies with the skin care product and a second set of activity metrics, activity data, product use metrics and product use event data for a second set of users who did not improve their cosmetic deficiencies with the skin care product;
      generate user feedback information based on the machine learning model to assist the user with the product usage of the skin care product or related skin care products based on the product use event data for the skin care product and the user profile data for the user; and
      provide the user feedback information via the user interface or the communication interface to a mobile device of the user;
      wherein to obtain an indication of product usage of the skin care product and identify the skin care product based on the obtained indication of product usage of the skin care product, the instructions cause the computing device to receive, via the communication interface, a communication signal from the skin care product, the communication signal including identification information for the skin care product;
      wherein the skin care product includes a communication component without a power source that provides the communication signal, and wherein the computing device provides electromagnetic signals to the communication component to power the communication component.

2. The computing device of claim 1, further comprising a camera, wherein the instructions cause the computing device to capture an image of an area within a field of view of the camera, identify an object within the image, determine visual characteristics of the identified object, and identify the skin care product based on the visual characteristics for the identified object in order to obtain an indication of product usage of the skin care product and identify the skin care product based on the obtained indication of product usage of the skin care product.

3. The computing device of claim 2, wherein the visual characteristics for the identified object include at least one of: a product tag, a product label, a product color, a product shape, a product size, or a product logo.

4. The computing device of claim 2, wherein to identify the skin care product based on the visual characteristics for the identified object, the instructions cause the computing device to:
   compare the visual characteristics for the identified object to a plurality of sets of visual characteristics, wherein each set of visual characteristics corresponds to a template skin care product of a plurality of template skin care products,
   identify a template skin care product of the plurality of template skin care products having a set of visual characteristics matching the visual characteristics for the identified object, and
   identify the skin care product corresponding to the template skin care product.

5. The computing device of claim 2, wherein to identify the skin care product based on the visual characteristics for the identified object, the instructions cause the computing device to identify the skin care product based on the visual characteristics for the identified object using one or more machine learning techniques.

6. The computing device of claim 1,
wherein the user profile data includes at least one of biographical information regarding the user, a current location of the user, an image of the user, and user preferences or goals regarding the skin care product.

7. The computing device of claim 6, wherein at least some of the user profile data includes information obtained from a questionnaire presented to the user via at least one of the user interface, the communication interface and the mobile device.

8. The computing device of claim 1, wherein the user feedback information includes at least one of: (i) rewards based on the product usage of the skin care product, (ii) a recommendation to replenish the skin care product, (iii) advice on the product usage of the skin care product, (iv) a recommendation to purchase related skin care products, (v) information regarding an amount of product usage of the skin care product by the user, (vi) information regarding an appropriate amount of product usage of the skin care product, (vii) performance information for the user regarding the product usage, behavioral choices, or results for the skin care product over time, (viii) information regarding combinations of skin care products used in a routine which indicate synergies or lack thereof, or (ix) a recommendation on how to improve the product usage of the skin care product by the user based on one or more of: the amount of product usage of the skin care product by the user, the appropriate amount of product usage of the skin care product, or the performance information regarding the product usage of the skin care product by the user.

9. The computing device of claim 1, wherein to generate user feedback information, the instructions cause the computing device to provide the product use event data and identification information for the user to a server device and receive the user feedback information from the server device, wherein the server device generates the user feedback information based on the product usage of the skin care product over time and the user profile data for the user.

10. The computing device of claim 1, further comprising a speaker, wherein the instructions cause the computing device to provide the user feedback information to the user via the speaker.

11. A method of providing feedback regarding skin care products, the method comprising:
obtaining, at a computing device, an indication of product usage of a skin care product by a user;
identifying, by the computing device, the skin care product based on the obtained indication of product usage of the skin care product;
obtaining, by the computing device, product use event data associated with the user for the skin care product, the product use event data comprises one or more of the following: a time in which the user used the skin care product, a date in which the user used the skin care product, an order in which the user used the skin care product relative to other skin care products, indications of the other skin care products used with the skin care product, a duration in which the user used the skin care product, and/or a manner in which the user used the skin care product, or a combination thereof;
generate a machine learning model for identifying skin care products; wherein the machine learning model is trained using a first set of activity metrics, activity data, product use metrics and product use event data for a first set of users who improved their cosmetic deficiencies with the skin care product and a second set of activity metrics, activity data, product use metrics and product use event data for a second set of users who did not improve their cosmetic deficiencies with the skin care product;
obtaining, by the computing device, user profile data for a user profile of the user;
generating based on the machine learning model user feedback information to assist the user with the product usage of the skin care product or related skin care products based on the product use event data for the skin care product and the user profile data for the user; and
providing, by the computing device, the user feedback information via a user interface or a communication interface to a mobile device of the user;
wherein obtaining an indication of product usage of the skin care product and identifying the skin care product includes receiving, by the computing device, a communication signal from the skin care product, the communication signal including identification information for the skin care product;
wherein the skin care product includes a communication component without a power source that provides the communication signal, and wherein the computing device provides electromagnetic signals to the communication component to power the communication component.

12. The method of claim 11, wherein obtaining an indication of product usage of the skin care product and identifying the skin care product includes capturing, by the computing device, an image of an area within a field of view of a camera included in the computing device, identifying, by the computing device, an object within the image, determining, by the computing device, visual characteristics of the identified object; and identifying, by the computing device, the skin care product based on the visual characteristics for the identified object.

13. The method of claim 11, wherein generating the user feedback information includes providing, by the computing device, the product use event data and identification information for the user to a server device, and receiving, by the computing device, the user feedback information from the server device, wherein the server device generates the user feedback information based on the product usage of the skin care product over time and the user profile data for the user.

* * * * *